United States Patent
Young (10) Patent No.: US 10,524,718 B2
(45) Date of Patent: *Jan. 7, 2020

(54) DEFORMITY CORRECTION USING NEURAL INTEGRITY MONITORING

(71) Applicant: Warsaw Orthopedic, Inc., Warsaw, IN (US)

(72) Inventor: John Stewart Young, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 697 days.

This patent is subject to a terminal disclaimer.

(21) Appl. No.: 15/015,941

(22) Filed: Feb. 4, 2016

(65) Prior Publication Data

US 2016/0151098 A1 Jun. 2, 2016

Related U.S. Application Data

(60) Division of application No. 13/295,288, filed on Nov. 14, 2011, now Pat. No. 9,278,214, which is a continuation of application No. 11/799,017, filed on Apr. 30, 2007, now Pat. No. 8,075,601.

(51) Int. Cl.
| | | |
|---|---|---|
| *A61B 5/05* | (2006.01) | |
| *A61N 1/36* | (2006.01) | |
| *A61B 17/00* | (2006.01) | |
| *A61B 5/00* | (2006.01) | |
| *A61B 17/70* | (2006.01) | |
| *A61B 17/02* | (2006.01) | |

(52) U.S. Cl.
CPC ........ *A61B 5/4041* (2013.01); *A61B 17/7092* (2013.01); *A61N 1/3604* (2017.08); *A61B 5/05* (2013.01); *A61B 5/4893* (2013.01); *A61B 2017/00039* (2013.01); *A61B 2017/0262* (2013.01)

(58) Field of Classification Search
CPC ... A61B 5/09; A61B 5/4893; A61B 2017/025; A61B 2017/0256; A61B 2017/062; A61B 2017/564; A61B 2017/565; A61B 17/70; A61B 17/7002; A61B 17/701; A61B 17/7011; A61B 17/7022; A61B 17/7032; A61B 17/7037; A61B 17/7038; A61B 17/7041; A61B 17/7053; A61B 17/7091; A61B 17/7092

See application file for complete search history.

(56) References Cited

U.S. PATENT DOCUMENTS

| | | |
|---|---|---|
| 4,616,660 A | 10/1986 | Johns |
| 4,713,506 A | 12/1987 | Klink |
| 4,823,791 A | 4/1989 | D'Amello et al. |

(Continued)

*Primary Examiner* — Adam J Eiseman (57) ABSTRACT

A method is provided for detecting neural interference between a bone anchor and a neural element during or subsequent to the application of force on the bone anchor to adjust the orientation of one or more vertebral bodies relative to the spinal column. The method includes engaging at least one bone anchor to the vertebral body and applying force to the bone anchor to adjust the positioning or orientation of the vertebral body. A nerve monitoring system provides an electrical signal and is operable to detect a neural element and its proximity to the bone anchor as a function of a characteristic of the electrical signal.

20 Claims, 8 Drawing Sheets

(56) References Cited

U.S. PATENT DOCUMENTS

| | | |
|---|---|---|
| 4,962,766 A | 10/1990 | Herzon |
| 5,026,370 A | 6/1991 | Lottick |
| 5,306,275 A | 4/1994 | Bryan |
| 5,474,558 A | 12/1995 | Neubardt |
| 5,782,831 A | 7/1998 | Sherman et al. |
| 6,251,111 B1 * | 6/2001 | Barker ............... A61B 17/7041 606/86 A |
| 6,299,613 B1 | 10/2001 | Ogilvie et al. |
| 6,551,320 B2 | 4/2003 | Lieberman |
| 6,554,778 B1 | 4/2003 | Fleming |
| 7,207,949 B2 | 4/2007 | Miles et al. |
| 7,470,236 B1 | 12/2008 | Kelleher et al. |
| 7,522,953 B2 | 4/2009 | Kaula et al. |
| 7,582,058 B1 | 9/2009 | Miles et al. |
| 7,657,308 B2 | 2/2010 | Miles et al. |
| 7,664,544 B2 | 2/2010 | Mlles et al. |
| 7,691,057 B2 | 4/2010 | Mlles et al. |
| 7,693,562 B2 | 4/2010 | Marino et al. |
| 7,785,253 B1 | 8/2010 | Arambula et al. |
| 7,819,801 B2 | 10/2010 | Miles et al. |
| 7,892,173 B2 | 2/2011 | Miles et al. |
| 7,905,840 B2 | 3/2011 | Pimenta et al. |
| 7,920,922 B2 | 4/2011 | Gharib et al. |
| 7,935,051 B2 | 5/2011 | Miles et al. |
| 7,942,826 B1 | 5/2011 | Scholl et al. |
| 7,962,191 B2 | 6/2011 | Marino et al. |
| 7,963,927 B2 | 6/2011 | Kelleher et al. |
| 7,991,463 B2 | 8/2011 | Kelleher et al. |
| 8,000,782 B2 | 8/2011 | Gharlb et al. |
| 8,005,535 B2 | 8/2011 | Gharib et al. |
| 8,016,767 B2 | 9/2011 | Miles et al. |
| 8,027,716 B2 | 9/2011 | Gharib et al. |
| 8,050,769 B2 | 11/2011 | Gharib et al. |
| 8,055,349 B2 | 11/2011 | Gharib et al. |
| 8,068,912 B2 | 11/2011 | Kaula et al. |
| 8,090,436 B2 | 1/2012 | Hoey et al. |
| 2002/0161372 A1 | 10/2002 | Bolger et al. |
| 2004/0106921 A1 | 6/2004 | Cheung et al. |
| 2004/0225228 A1 | 11/2004 | Ferree |
| 2005/0010300 A1 | 1/2005 | Disilvestro et al. |
| 2005/0075578 A1 | 4/2005 | Gharib et al. |
| 2005/0085743 A1 | 4/2005 | Hacker et al. |
| 2005/0182454 A1 | 8/2005 | Gharib et al. |
| 2006/0047282 A1 | 3/2006 | Gordon |
| 2006/0111767 A1 | 5/2006 | Olson et al. |
| 2006/0149236 A1 * | 7/2006 | Barry ................ A61B 17/7077 606/86 A |
| 2006/0173374 A1 | 8/2006 | Neubardt et al. |
| 2006/0173456 A1 | 8/2006 | Hawkes et al. |
| 2006/0173521 A1 | 8/2006 | Pond, Jr. et al. |
| 2006/0178593 A1 | 8/2006 | Neubardt et al. |
| 2006/0178594 A1 | 8/2006 | Neubardt et al. |
| 2008/0125637 A1 | 5/2008 | Geist et al. |
| 2009/0125072 A1 | 5/2009 | Neubardt |
| 2010/0094115 A1 | 4/2010 | Pond, Jr. et al. |
| 2010/0100011 A1 | 4/2010 | Roche |

* cited by examiner

DEFORMITY CORRECTION USING NEURAL INTEGRITY MONITORING

This application is a divisional application of U.S. patent application Ser. No. 13/295,288, filed Nov. 14, 2011, now allowed, which is a continuation of prior application Ser. No. 11/799,017, filed Apr. 30, 2007, now U.S. Pat. No. 8,075,601. These applications are incorporated herein by reference, in their entireties.

BACKGROUND

Surgery for a patient can be painful and traumatic, particularly in the affected area of the patient's body. For spinal fixation systems, a necessary procedure often involves forming a hole in a pedicle of a vertebra in a patient's spine and inserting a spinal pedicle screw into the hole. Pedicle screws are advantageous in that they are strong and provide stability, however, care must be taken to avoid nerve impingement during formation of the holes and the placement of pedicle screws in the vertebral body. Some measures taken range from monitoring muscle reactions to electrically stimulating tissue to locate nerves in or adjacent the bone tissue during preparation of the hole and during insertion of the pedicle screw.

Some spinal procedures further require a force to be applied to one or more inserted pedicle screws to change the orentation of one or more vertebrae and/or to align the pedicle screw for connection with other components of a spinal fixation system. The application of additional forces on the pedicle screw can sometimes weaken or compress the bone surrounding the screw, potentially exposing neural elements to the pedicle screw. If the screw contacts an exposed nerve, impinges on the nerve, or becomes too close to the nerve root, pain and other implications for the patient may result.

SUMMARY

Instruments and methods are provided that are employed to locate or detect neural elements during or subsequent to the exertion of vertebral body orientation changing forces on one or more pedicle screws. One aspect is a unique surgical method. Other aspects include unique systems, devices, instrumentation, and apparatus involving an orthopedic implantable device system.

In one aspect, there is a surgical method that includes providing a bone anchor; engaging the bone anchor to a location on a vertebral body when the vertebral body is in a first orientation; coupling the bone anchor with a correction tool; manipulating the correction tool to move the vertebral body with the bone anchor toward a second orientation; and electrically monitoring the bone anchor with a nerve monitoring system to detect interference between a neural element and the bone anchor while the vertebral body is moved toward the second orientation.

In a further aspect, there is provided a surgical method which includes forming a bone anchor hole at a first location into a vertebral body of a spinal column; providing a bone anchor; engaging the bone anchor to the vertebral body in the bone anchor hole; providing a correction tool; coupling the correction tool with the bone anchor providing a nerve monitoring system; coupling the nerve monitoring system to the correction tool; applying force to the bone anchor with the correction tool to change an orientation of the vertebral body relative to the spinal column while detecting for interference between a neural element and the bone anchor with the nerve monitoring system; detecting interference between the neural element and the bone anchor with the nerve monitoring system; and applying force to at least one of a second location on the vertebral body and an adjacent vertebral body with the correction tool to change the orientation of the spinal column after detecting interference between the neural element and the bone anchor.

Still in another aspect, there is provided a surgical method that includes preparing a bony tissue area of a vertebra for reception of a bone anchor when the vertebra is in a first position; electrically coupling a nerve monitoring system to a bone anchor driver, engaging the bone anchor with the bone anchor driver to engage the bone anchor to the prepared bony tissue area of the vertebra while providing an electrical signal to the bone anchor through the bone anchor driver, detecting a neural element threshold as a function of the electrical signal with the nerve monitoring system while engaging the bone anchor to the bony tissue area; engaging the bone anchor with a correction tool; electrically coupling the correction tool with the nerve monitoring system; moving the correction tool while engaged to the bone anchor to change an orientation of the vertebra to a second position from the first position; and providing an electrical signal through the correction tool to the bone anchor to detect a neural element threshold as a function of the electrical signal with the nerve monitoring system while changing the orientation of the vertebra.

Yet another aspect includes providing a first bone anchor and a second bone anchor, engaging the first bone anchor to a first location on a first vertebral body of a spinal column when the first vertebral body is at a first orientation relative to the spinal column and engaging the second bone anchor to a second location on the first vertebral body of the spinal column; interconnecting the first bone anchor with the second bone anchor; coupling a correction tool to at least one of the first and second bone anchors; and monitoring the proximity of the at least one of first and second bone anchors with a nerve monitoring system to detect interference with a neural element while the first vertebral body is moved toward the second orientation.

Further embodiments, forms, features, aspects, benefits, objects, and advantages of the present application shall become apparent from the detailed description and figures provided herewith.

DETAILED DESCRIPTION OF SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

A surgical method is provided that includes engaging one or more anchors to at least one vertebra of a spinal column. The at least one vertebra is misaligned with the spinal column such that its orientation requires changing by moving, translating, rotating, pivoting or otherwise adjusting the position of the at least one vertebra relative to the other vertebrae of the spinal column. A deformity correction tool is engaged to the at least one vertebra by either mounting the tool to the anchor, to an extension extending from the anchor, to a connecting element extending between anchors engaged to the misaligned vertebrae, or to a connecting element extending between vertebrae of the spinal column. The correction tool is manipulated to change the orientation of the misaligned vertebra to a desired position relative to the spinal column. The correction tool can be any suitable vertebral column manipulator device or system. Further examples are provided in U.S. patent application Ser. Nos. 11/350,914 and 11/350,915, each of which was filed on Feb. 9, 2007 and each of which is hereby incorporated by reference.

The correction tool is coupled to a nerve monitoring system that allows the surgeon or other attendant to monitor nerve activity that results as correctional forces are applied to the misaligned vertebra through the anchor engaged thereto. If the nerve monitoring system indicates that a neural element is adversely affected during the manipulation of the misaligned vertebra, the surgical procedure can be altered or appropriate measures taken to avoid trauma to the neural elements.

Figure 1:
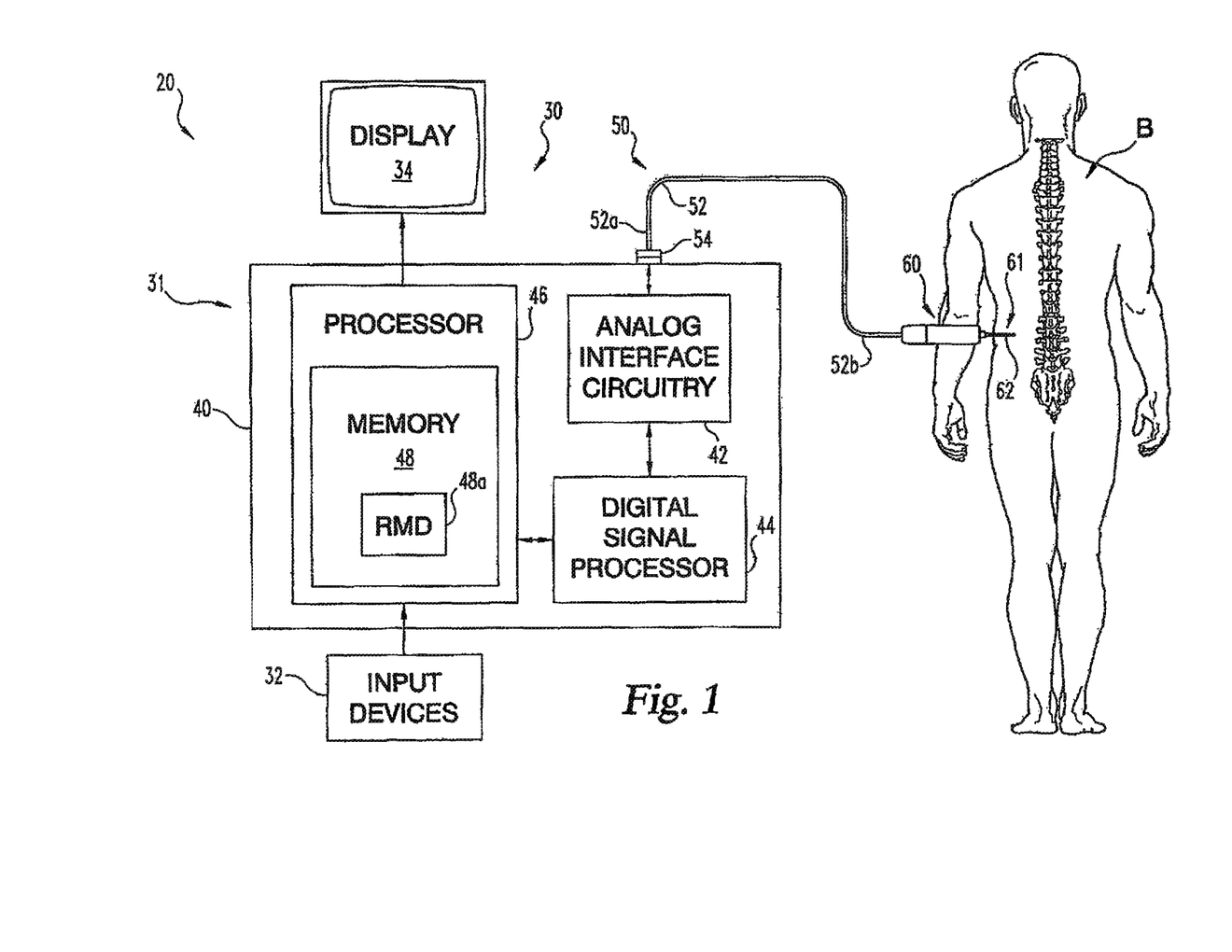
FIG. 1 is a schematic diagram of a surgical system.

FIG. 1 illustrates system 20 that includes a medical tool and associated equipment arranged to provide medical treatment. System 20 is employed to correct a deformity in one or more vertebrae of spinal column B. Further, system 20 is operable to provide nerve monitoring and to detect interference between various components of the tools and implants positioned into a vertebral body and neural elements in spinal column B. Upon detection of interference between the tool and/or implant and a neural element, system 20 notifies a user of such occurrence so that appropriate remedial or corrective action can be taken during the surgical procedure.

System 20 includes a nerve monitoring system 30, a connection link 50, and a medical tool 60. Nerve monitoring system 30 includes equipment 31 coupled to tool 60 with connection link 50. Alternatively, equipment 31 may be integrated into tool 60 as a stand alone nerve monitoring tool. Tool 60 is configured for operation relative to a spinal pedicle wall of spinal column B of a human patient or subject, such as represented in FIG. 1. One example of a suitable nerve monitoring system 30 is the NIM-Spine® System marketed by Medtronic, Inc., although applications with other nerve monitoring systems are also contemplated.

Equipment 31 includes operator input devices 32, operator display device 34, and various other operator-utilized equipment of system 20 that is external to a patient during use. Input devices 32 may include an alphanumeric keyboard and mouse or other pointing device of a standard variety. Alternatively or additionally, one or more other input devices can be utilized, such as a voice input subsystem or a different type as would occur to those skilled in the art. Operator display device 34 can be of a Cathode Ray Tube (CRT) type, Liquid Crystal Display (LCD) type, plasma type, Organic Light Emitting Diode (OLED) type, or such different type as would occur to those skilled in the art. Alternatively or additionally, one or more other operator output devices can be utilized, such as a printer, one or more loudspeakers, headphones, or such different type as would occur to those skilled in the art. Nerve monitoring system 30 also can include one or more communication interfaces suitable for connection to a computer network, such as a Local Area Network (LAN), Municipal Area Network (MAN), and/or Wide Area Network (WAN) like the internet a medical diagnostic device; another therapeutic device; a medical imaging device; a Personal Digital Assistant (PDA) device; a digital still image or video camera; and/or audio device, to name only a few. Nerve monitoring system 30 can be arranged to show other information under control of the operator.

Equipment 31 may also include processing subsystem 40 for processing signals and data associated with system 20. Subsystem 40 may include analog interface circuitry 42, Digital Signal Processor (DSP) 44, data processor 46, and memory 48. Analog interface circuitry 42 can be responsive to control signals from DSP 44 to provide corresponding analog stimulus signals to tool 60. At least one of analog interface circuitry 42 and DSP 44 may include one or more digital-to-analog converters (DAC) and one or more analog-to-digital converters (ADC) to facilitate operation of system 20 in the manner to be described in greater detail hereinafter. Processor 46 can be coupled to DSP 44 to bidirectionally communicate therewith, selectively provide output to display device 34, and selectively respond to input from operator input devices 32.

DSP 44 and/or processor 46 can be of a programmable type; a dedicated, hardwired state machine; or a combination of these. DSP 44 and processor 46 perform in accordance with operating logic that can be defined by software programming instructions, firmware, dedicated hardware, a combination of these, or in a different manner as would occur to those skilled in the art. For a programmable form of DSP 44 or processor 46, at least a portion of this operating logic can be defined by instructions stored in memory 48. Programming of DSP 44 and/or processor 46 can be of a standard, static type; an adaptive type provided by neural networking, expert-assisted learning, fuzzy logic, or the like; or a combination of these.

Memory 48 is illustrated in association with processor 46; however, memory 48 can be separate from or at least partially included in one or more of DSP 44 and processor 46. Memory 48 includes at least one Removable Memory Device (RMD) 48a. Memory 48 can be of a solid-state variety, electromagnetic variety, optical variety, or a combination of these forms. Furthermore, memory 48 can be volatile, nonvolatile, or a mixture of these types. Memory 48 can be at least partially integrated with circuitry 42, DSP 44, and/or processor 46. RMD 48a can be a floppy disc, cartridge, or tape form of removable electromagnetic recording media; an optical disc, such as a CD or DVD type; an electrically reprogrammable solid-state type of nonvolatile memory, and/or such different variety as would occur to those skilled in the art. In still other embodiments, RMD 48a is absent.

Circuitry 42, DSP 44, and processor 46 can be comprised of one or more components of any type suitable to operate as described herein. Further, it should be appreciated that all or any portion of circuitry 42, DSP 44, and processor 46 can be integrated together in a common device, and/or provided as multiple processing units. For a multiple processing unit form of DSP 44 or processor 46; distributed, pipelined, and/or parallel processing can be utilized as appropriate. In one embodiment, circuitry 42 is provided as one or more components coupled to a dedicated integrated circuit form of DSP 44; processor 46 is provided in the form of one or more general purpose central processing units that interface with DSP 44 over a standard bus connection; and memory 48 includes dedicated memory circuitry integrated within DSP 44 and processor 46, and one or more external memory components including a removable disk form of RMD 48a. Circuitry 42, DSP 44, and/or processor 46 can include one or more signal filters, limiters, oscillators, format converters (such as DACs or ADCs), power supplies, or other signal operators or conditioners as appropriate to operate system 20 in the manner to be described in greater detail hereinafter.

In one embodiment, connection link 50 includes a link 52 in the form of a flexible cable with a proximal end 52a and an opposite distal end 52b. A connector 54 is electrically connected to equipment 31 of nerve monitoring system 30. Link 52 extends from connector 54 at proximal end 52a to distal end 52b where it is connected with medical tool 60. Connection link 50 may include forms in addition to or in alternative to link 52, including one or more wires, cords, wireless links, infrared components, bluetooth, or other communication link. Further, it should be appreciated that other components, devices, and systems can be integrated into system 20, such as an endoscope system, a catheterization system, an imaging system, a lighting system, and/or a video camera system, to name a few examples. Connection link 50 and tool 60 are movable toward and away from spinal column B in a surgical procedure that may include one or more of retractors, tubes, sleeves, guards, microincisions or other components not shown to enhance clarity.

Figure 2:
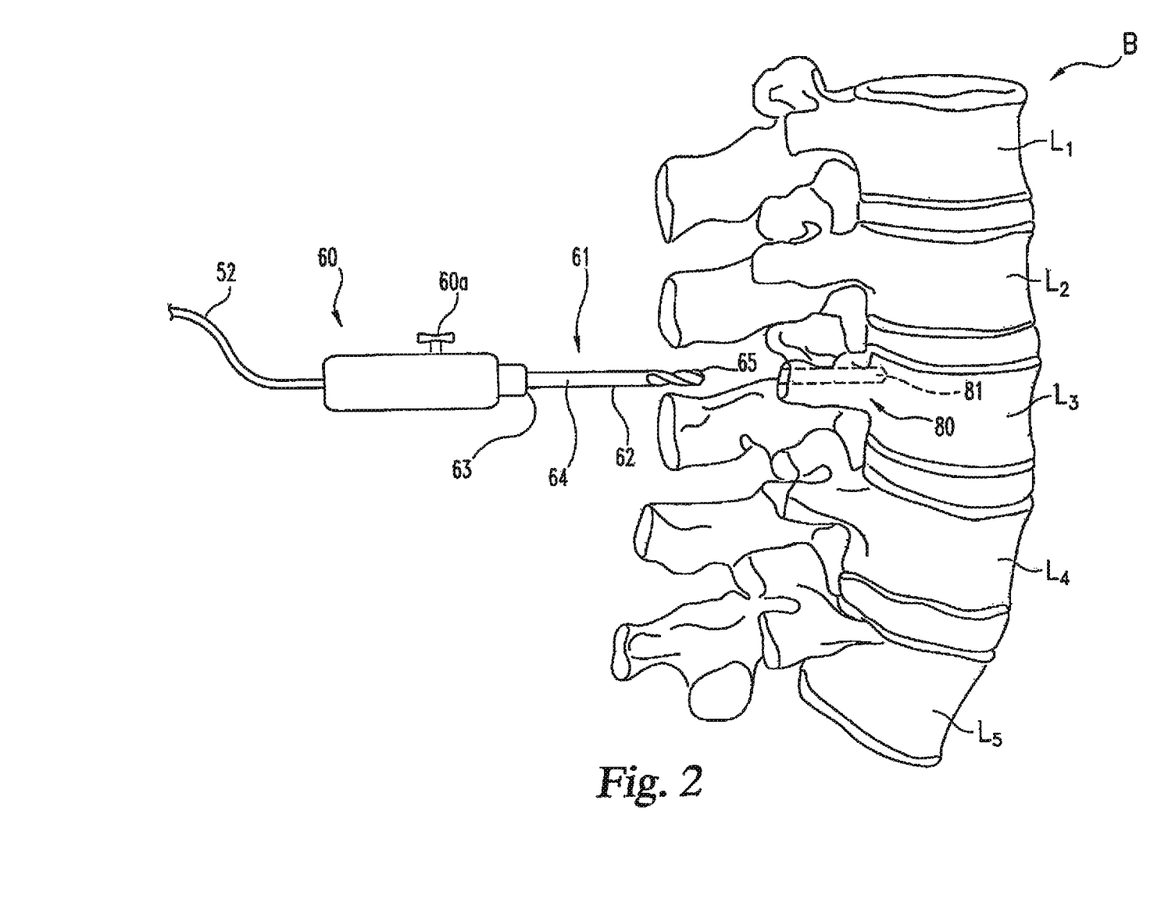
FIG. 2 is a diagrammatic view of a boring tool relative to a section of the spine.
Figure 3:
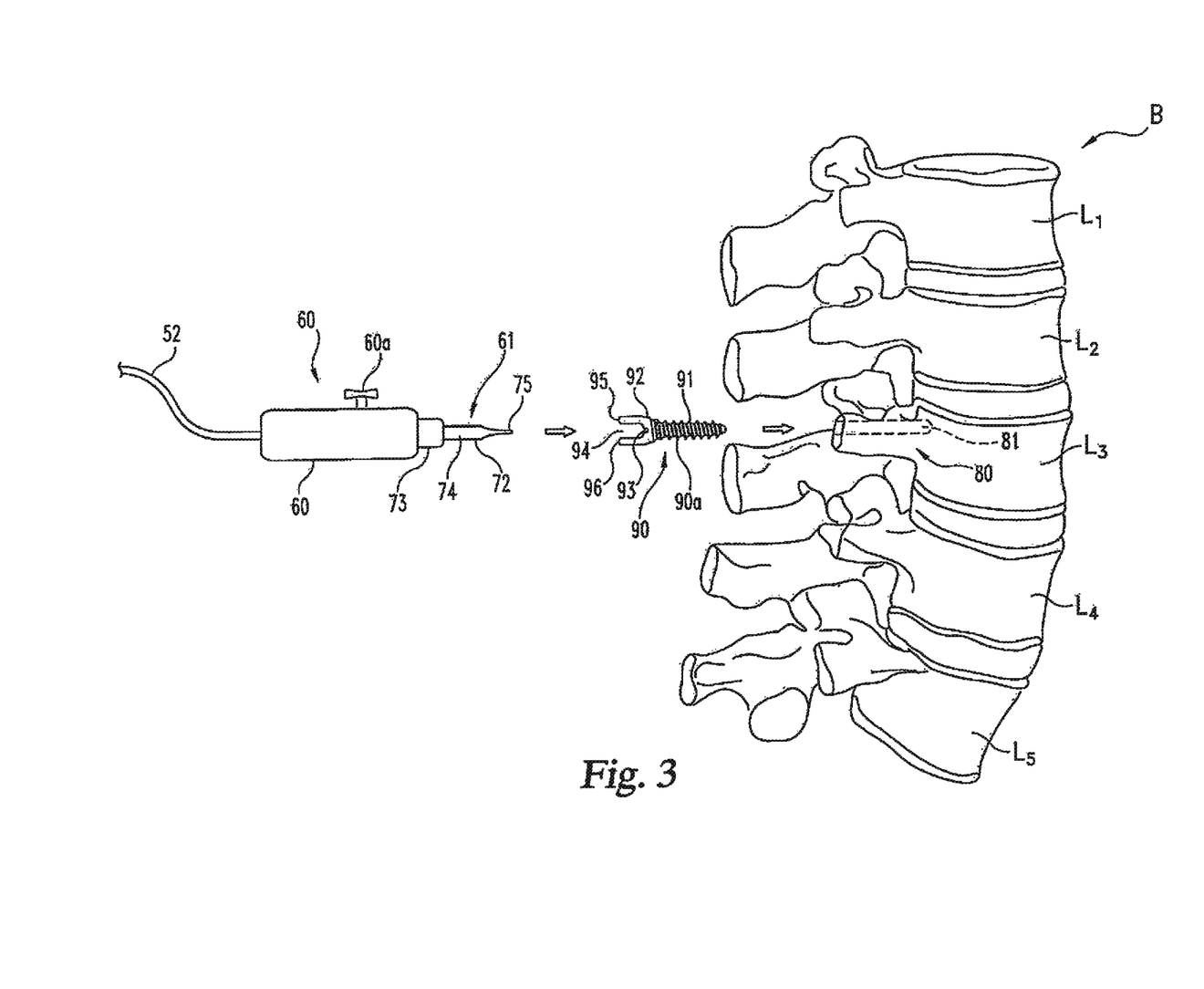
FIG. 3 is a diagrammatic view of an anchor driver relative to a section of the spine.

Various embodiments of tool 60 are shown in FIGS. 2 and 3 relative to a prepared Implant site 80 on vertebra $L_3$, as viewed laterally from the right side of a patient. It should be understood that throughout the figures associated herewith, system 20, tool 60, and implants 90 are shown relative to the lumber region of spinal column B, including vertebral bodies $L_1$-$L_5$. It should be understood that the lumbar region has been shown for illustrative purposes only, and that the systems and methods discussed herein may be applied to any region or vertebral body of spinal column B.

In FIGS. 1 and 2, tool 60 includes a working portion 61 in the form of a bit 62 suitable for use as a drill to cut and remove bone material to form a hole to receive a bone anchor. Bit 62 includes a universal connector 63 at its proximal end, a shaft 64, and a non-insulated cutting tip 65 at a distal end. Universal connector 63 may include any suitable configuration for releasable connection with tool 60. Tool 60 includes a user control 60a which may be depressed to supply rotary movement to bit 62 in order to prepare anchor hole 81, as shown in phantom in both FIGS. 2 and 3. As illustrated, hole 81 is formed in a pedicle wall, but it should be understood that one having ordinary skill in the art would appreciate that hole 81 may be formed at any suitable location on a vertebral body.

In FIG. 3, another embodiment of tool 60 is shown with a working portion 61 in the form of a driver 72 including a universal connector 73 at its proximal end, a shaft 74, and a non-insulated tip 75 at a distal end. As illustrated, tip 75 of screwdriver 72 is proximal to implant 90 in the form of bone anchor 90a. In the illustrated embodiment, bone anchor 90a includes a longitudinal helically threaded stem 91 and a head portion 92. Stem 91 is structured to threadingly engage a passageway prepared in one or more bones or bony structures in a standard manner, and can be provided with cutting flutes or other structure for self-tapping and/or self-drilling capabilities. Stem 91 can also be cannulated to receive a guidewire to facilitate placement and may further include fenestrations or other openings for placement of bone growth material. Other embodiments contemplate bone anchors with other bone engaging arrangements for engaging bony tissue of the vertebra, including non-threaded arrangements.

Head portion 92 includes a tool engagement portion 93 and various other features, including for example, a receiving channel 94 between arms 95, 96. Arms 95, 96 can be internally and/or externally threaded or include any other suitable arrangement to engage a set screw, nut, cap or other device for securing the connecting element in the channel. Other arrangements for head portion 92 are also contemplated, including a proximally extending post that is smooth or threaded, a rounded or flat head, or any other suitable configuration. Tool engagement portion 93 may be of any suitable shape or configuration, including being formed as an internal recess or as an external shape for engagement with a driving tool or correction tool. Examples include slotted, Phillips, square, hex, Torx®, etc., and it should be understood that the shape or configuration of tip 75 corresponds to the shape of tool engagement portion 93 to facilitate a mating engagement therebetween.

When tip 75 is engaged with bone anchor 90a, tool 60 is operable to supply a rotary force to implant bone anchor 90a into hole 81. It should be further understood that bone anchor 90a may be, but is not limited to being, a multi-axial, poly-axial, uni-axial, or uni-planar bone screw where stem 91 and head portion 92 are movable relative to one another. Furthermore, in one form bone anchor 90a is made of medical grade stainless steel, but in other embodiments may be comprised of, but is not limited to, titanium, a titanium alloy or other metallic alloy, and/or a nonmetallic composition.

In the illustrations of both FIGS. 2 and 3, tool 60 is coupled with link 52 of nerve monitoring system 30. Nerve monitoring system 30 is operable to detect interference between bit 62 and a neural element during preparation of hole 81 indicating an exposure, encroachment or close proximity of a neural element in prepared hole 81. Using the implant driver 72, nerve monitoring system 30 is operable to detect Interference, encroachment or close proximity between bone anchor 90a and a neural element during and after insertion of bone anchor 90a into hole 81. In some embodiments, upon detection of interference with or exposure of a neural element, nerve monitoring system 30 may terminate the power supply to tool 60 to stop the movement of tool portion 61 to avoid further potential for damaging the neural element. Additional information regarding neural element detection is set forth in U.S. Pat. No. 5,474,558 to Neubardt; U.S. Patent Publication No. 2006/0178593 to Neubardt et al.; U.S. Patent Publication No. 2006/0178594 to Neubardt at al.; U.S. Patent Publication No. 2006/0173521 to Pond et al.; and U.S. Patent Publication No. 2006/0173374 to Neubardt et al., each of which is incorporated herein by reference in its entirety.

Nerve monitoring system 30 generally supplies to tool 60 an electrical signal used to locate neural elements that are proximate to working portion 61. For example, an electrical lead can extend from working portion 61, through tool 60, to nerve monitoring system 30 for coupling with a source of electrical current either separately from or as a part of connection ink 50. In FIG. 2, the electrical current is delivered to tip 65 to allow monitoring and detection of neural elements based on the proximity and response of the neural elements to the electrical signal. During creation of hole 81, tip 65 carries an electrical signal that provides an indication of the proximity of neural elements in the bone tissue relative to tip 65 during formation of hole 81. In FIG. 3, the electrical current is delivered to tip 75 and to bone anchor 90a, such that bone anchor 90a carries the electrical signal that provides an indication of the proximity of neural elements in the bone tissue relative to bone anchor 90a during and after implantation into hole 81.

In another embodiment, the electric signal provides electrical stimulation to the tissue surrounding hole 81, and the patient response to the nerve stimulation is monitored to determine whether a neural element threshold has been reached. The threshold can correspond to, for example, an Indication of the presence of a neural element and/or its proximity relative to hole 81. In another embodiment, when the source of the electrical current, either tool portion 61 or bone anchor 90a, is positioned near or proximate a neural element, the presence of the neural element creates an electrical current path for the electrical signal. The current path provides an Indication to nerve monitoring system 30 of the presence of the neural element, and corrective action can then be taken by the surgeon based on this indication. In other words, detection of the neural element threshold occurs as a function of the electrical signal at tool portion 61 or bone anchor 90a, Inducing a reaction in the patient or particular reading at the threshold.

In some embodiments, the components of system 20 comprise an electrically conductive material surrounded by an insulative member or coating thereabout to prevent shunting of electricity delivered therethrough to adjacent tissue or devices. For example, link 52 and tool 60 may include an electrical pathway surrounded by an Insulative material. Furthermore, universal connectors 63, 73 and shafts 64, 74 are insulated while tips 65, 75 are not insulated. For shaft 63, this allows tip 65 to be exposed to adjacent bone tissue and carries an electrical signal for detection of nerve proximity thereabout. For shaft 73, this allows tip 75 to pass the current to bone anchor 90a. In some embodiments, the entire bone anchor 90a is not insulated, however, it is contemplated that parts of bone anchor 90a may be insulated to protect from interference from surrounding tissues or instruments or to monitor specific sections of hole 81.

Figure 4:
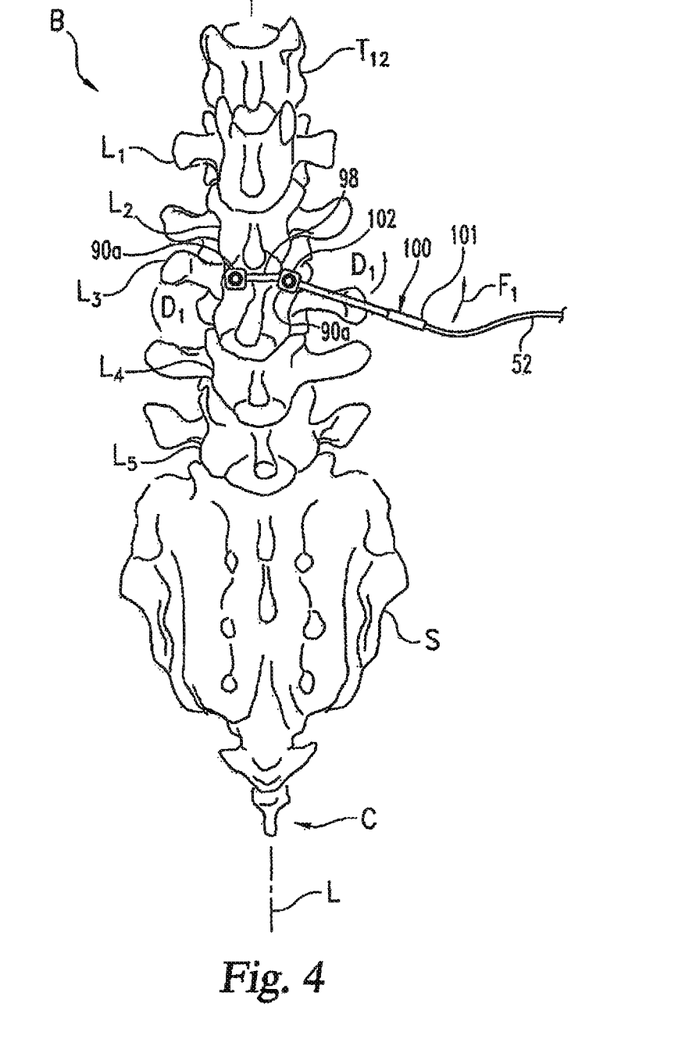
FIG. 4 is a posterior view of the spinal column of a patient that includes a misaligned vertebra and a diagrammatic view of a correction tool coupled to one or more bone anchors engaged to a misaligned vertebra.

Referring now to FIG. 4 there is shown from a posterior view a portion of the spinal column B of a patient Spinal column B includes the coccyx C and sacrum S just below the lumbar region of the spine including vertebra $L_1$-$L_5$. Immediately above vertebra $L_1$ is the lowest vertebra of the thoracic spine $T_{12}$. As shown from a posterior view in each of FIGS. 4 and 6, vertebra $L_3$ is mis-aligned such that its orientation relative to the rest of the spinal column B requires changing. It should be understood that the systems and methods discussed herein may be applied change the orientation of one vertebra or multiple vertebrae. The systems and methods discussed herein may also be applied to other regions of the spinal column B to correct numerous deformities associated therewith, like for example treatment of degenerative spondylolisthesis, fracture, dislocation, scoliosis, kyphosis, spinal tumor, and/or a failed previous fusion, just to name a few.

In FIG. 4 bone anchor 90a has been Inserted into hole 81 according to the system and method described hereinabove. In other embodiment, bone anchor 90a is inserted without nerve monitoring system 30 being employed. It is also contemplated that a second bone anchor 90a can be engaged to the pedicle of vertebra La on the contra-lateral side of the spinal column, and the anchor 90a connected with a cross-link connecting element 98. In other embodiments, only a single anchor 90a is engaged to vertebra $L_3$.

Bone anchor 90a is engaged by a correction tool 100 including a proximal end 101 and an opposite a distal end 102. Distal end 102 is engaged with bone anchor 90a. Any suitable arrangement for distal end 102 for engaging bone anchor 90a is contemplated. Examples include a distal end 102 with a clamping arrangement that clamps the anchor, a threaded connector that threadingly engages the connector, a sleeve that fits around all or a portion of the anchor, or an end member that fits in a receptacle of the anchor. Link 52 is electrically coupled to correction tool 100 at any suitable location, such as at proximal end 101, and tool 100 includes an electrical pathway so that an electrical signal from nerve monitoring system 30 may pass through correction tool 100 to bone anchor 90a. It is contemplated that all or part of correction tool 100 may include an insulative covering to prevent shunting of the electrical signal to other instruments and adjacent tissue. In still other embodiments, distal end 102 of correction tool 100 is engaged to cross link element 98.

Correction tool 100 extends from bone anchor 90a to a proximal handle positioned so that a correctional force $F_1$ may be applied to correction tool 100 which translates the force to bone anchor 90a to rotate, pivot, translate or otherwise move or Influence vertebral body $L_3$ to change its orientation into a desired alignment with the other vertebra of spinal column B. In the illustrated embodiment, correctional force $F_1$ is a rotational force that moves vertebra $L_3$ in a counter-clockwise direction $D_1$. Other correctional forces are also contemplated, including axial forces along tool 100 that translate vertebral body $L_3$ and pivoting forces created by pivoting tool 100 about Its distal end connection with bone anchor 90a.

As correctional force $F_1$ is applied, nerve monitoring system 30 supplies an electrical signal through link 52 and correction tool 100 to bone anchor 90a to continuously monitor, as described herein, neural Interference that might occur as a result of the correctional force applied to bone anchor 90a while embedded in vertebra $L_3$. If the application of the correctional force transfigures the orientation of bone anchor 90a in hole 81 or otherwise unsuitably exposes, impinges or encroaches on one or more neural elements, the nerve monitoring system 30 provides an indication of the same to the surgeon so that appropriate corrective action can be taken. In embodiments employing a cross-link connecting element 98, multiple locations can be monitored through multiple correction tools, or through a single correction tool electrically linked to multiple bone anchors via electrically conductive components connected between the bone anchors.

Figure 5:
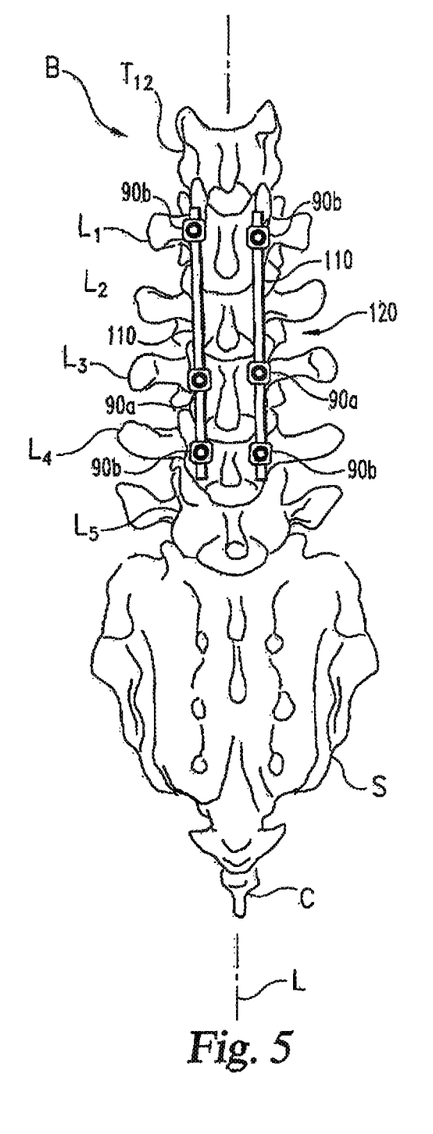
FIG. 5 is a posterior view of the spinal column of FIG. 4 with the misaligned vertebra moved into alignment with the spinal column and a spinal fixation system secured to the spinal column to maintain the corrected position of the vertebra.

Either before or after vertebra $L_3$ has been moved to change its orientation into proper alignment with spinal column B, additional bone anchors 90b may be engaged to other vertebrae of spinal column B as shown In FIG. 5. Bone anchor 90b may be of a type like that discussed above for bone anchor 90a, or for example, may be a laminar hook or include any other suitable bone engaging configuration that is embedded within or reside along a spinal element. Fixation system 120 also includes one or more connecting element(s) 110 that are used to interconnect anchors 90a and 90b to retain vertebra $L_3$ In alignment with spinal column B. Connecting elements 110 may be, for example, a spinal rod, tether, staple, cable, band, plate, or other suitable connecting element The connecting element may be solid or hollow along some or all of its length and/or may be of homogenous or heterogeneous composition. Additionally, connecting element 110 can be rigid, or be flexible or include one or more flexible portions to permit at least limited spinal motion when engaged along one or more vertebral levels of the spinal column.

While correction tool 100 is not shown coupled with bone anchor 90a in FIG. 5, it is contemplated that correction tool 100 or any of the other tools discussed herein may be coupled with bone anchor 90a during interconnection of the components of system 120 to provide detection of an Interference with a neural element through nerve monitoring system 30. It is further contemplated that correction tool 100 may be re-engaged with bone anchor 90a subsequent to interconnection and stabilization via connecting element 110 to detect for any neural element Interference. Additionally, it is contemplated that nerve monitoring system 30 may be connected to any bone anchor of system 120 to detect neural Interference.

Figure 6:
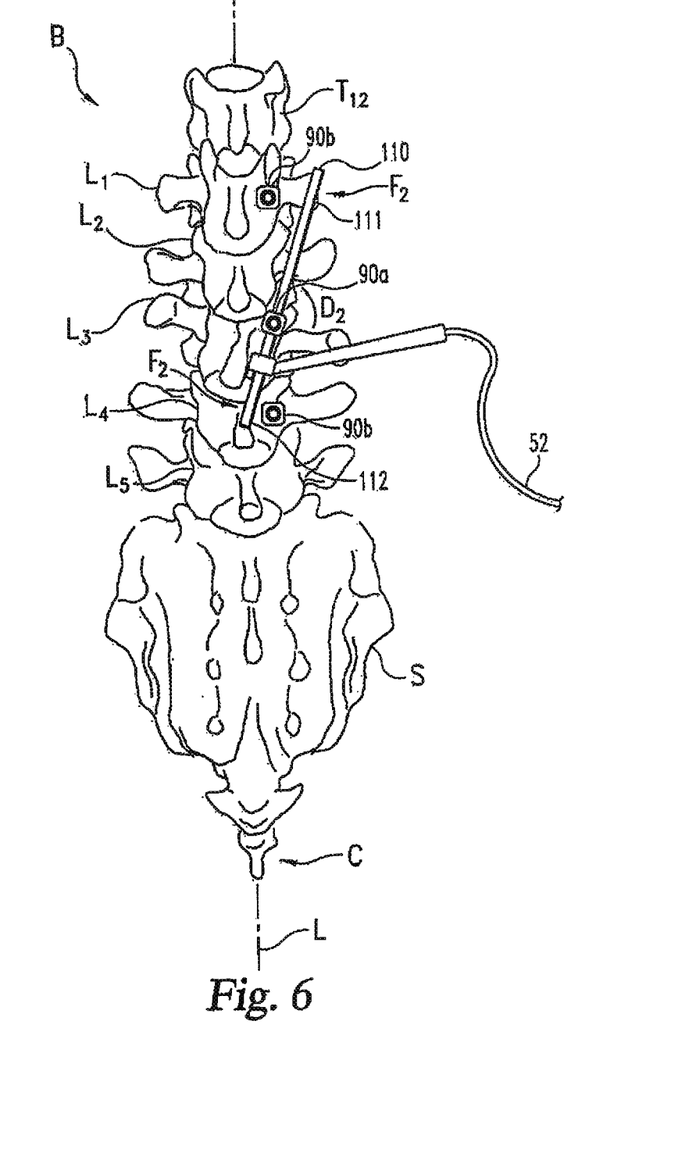
FIG. 6 is a posterior view of the spinal column of the patient including a misaligned vertebra and a diagrammatic view of a correction tool coupled to a connecting element extending along the spinal column and engaged to the misaligned vertebra.

Referring now to FIG. 6, there is shown in posterior view a portion of the spinal column B of a patient, where like numerals refer to like features previously described, in which vertebra $L_3$ is misaligned or otherwise requires its orientation relative to spinal column B to be adjusted. Bone anchor 90a is inserted into hole 81 and connecting element 110 has been connected to bone anchor 90a. Correction tool 100 is engaged to connecting element 110. Also connected to correction tool 100 is link 52 of nerve monitoring system 30. An electrical pathway is formed from tool 100 to bone anchor 90a via connecting element 110. Other embodiments contemplate that link 52 may be connected to bone anchor 90a in any way suitable to provide an electrical pathway from nerve monitoring system 30 to bone anchor 90a. For example, in one embodiment link 52 is directly connected to bone anchor 90a. In another embodiment, link 52 is attached to tool 60 including working portion 61, and working portion 61 is engaged with bone anchor 90a. In still other embodiment, link 52 is attached to instruments that are not employed as vertebral column manipulators. Examples of such Instruments include probes, retractors, guidewires, curettes, rongeurs, forceps, scalpels, scrapers, reamers, dilators, pushers, screw extenders, spreaders, and distractors, to name a few.

As correctional force $F_2$ is applied to connecting element 110, ends 111 and 112 of connecting element 110 are moved toward bone anchors 90b. The correctional force is translated to bone anchor 90a and vertebra La to rotate, translate, pivot or otherwise adjust the orientation of vertebra $L_3$ in a counter-clockwise direction to align vertebra $L_3$ with spinal column B. As the orientation of vertebra $L_3$ is corrected, nerve monitoring system 30 supplies an electrical signal to bone anchor 90a to detect any new neural Interference between bone anchor 90a and a neural element as a result of the force applied to bone anchor 90a.

In another embodiment, one of the ends 110, 112 of connecting element 110 is first connected to one of the bone anchors 90b. Correction tool 100 is engaged to connecting element 110 and linked to nerve monitoring system 30 with an electrical pathway formed from tool 100 to bone anchor 90b via connecting element 110. Other embodiments contemplate that link 52 may be connected to bone anchor 90b in any way suitable to provide an electrical pathway from nerve monitoring system 30 to bone anchor 90b. For example, in one embodiment link 52 is directly connected to bone anchor 90b. In another embodiment, link 52 is attached to tool 60 including working portion 61, and working portion 61 is engaged with bone anchor 90b.

Figure 7:
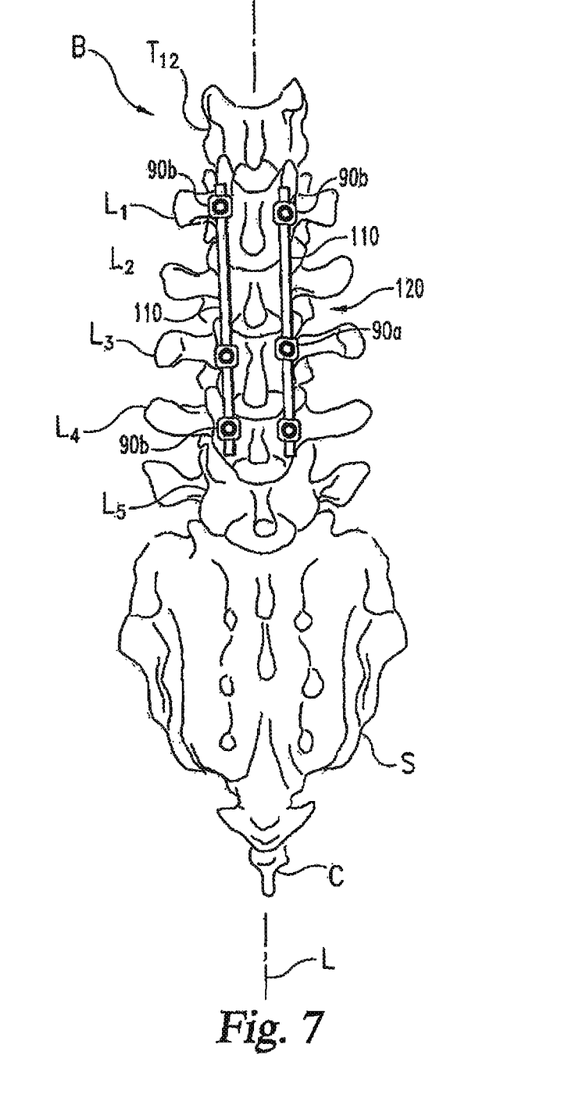
FIG. 7 is a posterior view of the spinal column of FIG. 6 with the misaligned vertebra moved into alignment with the spinal column and a spinal fixation system secured to the spinal column to maintain the corrected position of the vertebra.

As a correctional force is applied to connecting element 110, the other of the ends 111, 112 of connecting element 110 is moved toward the other bone anchor 90b and the middle of connecting element is moved toward bone anchor 90a. The correctional force is translated to bone anchor 90b connected to element 110 and to the vertebra in which the bone anchor 90b is engaged to rotate, translate, pivot or otherwise adjust the orientation of the engaged to align it in spinal column B. As the orientation of the superior or inferior-most vertebra is corrected, nerve monitoring system 30 supplies an electrical signal to bone anchor 90b to detect any new neural Interference between bone anchor 90b and a neural element as a result of the force applied to bone anchor 90b. The steps are then repeated as necessary along the spinal column from an adjacent vertebra to the next adjacent vertebra to segmentally reduce the vertebrae to the respective anchors FIG. 7 provides a posterior view of posterior fixation system 120, wherein like numerals refer to like features previously described, including bone anchor 90a, bone anchors 90b, and connecting elements 110. Vertebral body $L_3$ is oriented so that it is in alignment with spinal column B and is retained in alignment through interconnection by connecting elements 110 to bone anchors 90a and 90b. Link 52 can remain connected with bone anchor 90a or any of the other bone anchors to continue monitoring for neural interference until all adjustments have been made. Once fixation system 120 is completely implanted, link 52 may be disconnected and removed from bone anchor 90a. If, at some point during the implantation of fixation system 120, neural Interference occurs, a user may modify the location or orientation of the bone anchor into corresponding pedicle, or adjust the placement of any of the components of system 120.

Figure 8:
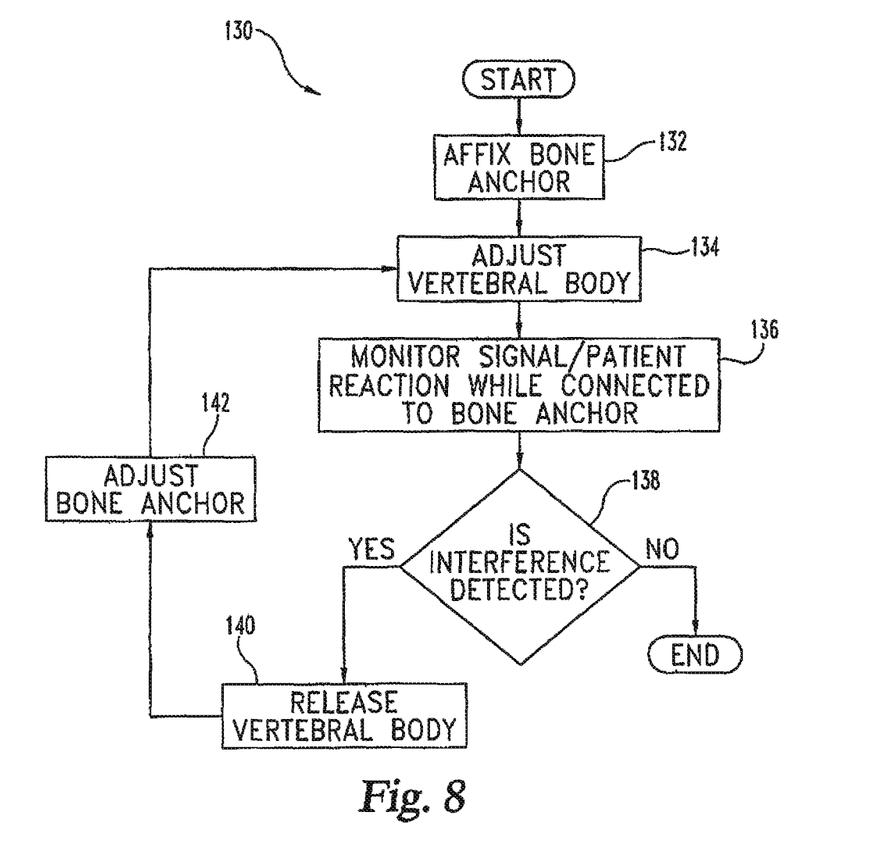
FIG. 8 is a flowchart of one embodiment diagnostic procedure that can be implemented with the system of FIG. 1.

An example of a surgical procedure 130 employing system 20 is provided in FIG. 8. At stage 132, at least one bone anchor 90a is engaged to a desired vertebral body and electrically coupled with the nerve monitoring system. A force is then applied to the at least one bone anchor 90a at stage 134 to translate the force from bone anchor 90a to the vertebral body to move or position the orientation of the vertebral body into alignment with spinal column B. After the vertebral body has been aligned, or during the movement of the vertebral body, nerve monitoring system 30 is used to monitor the electrical signal and patient reaction to detect any neural interference that might have occurred during stage 134 as force is applied to the at least one bone anchor.

If interference is not detected at stage 138 following stage 136, then the monitoring of neural element can end at 130 or be continued for one or more other anchors and/or vertebrae. If interference is detected at stage 138, then the vertebral body is released at stage 140 so that it is no longer being moved from its first orientation toward the second orientation in alignment with the spinal column. In certain situations the tissue connecting the vertebra to the other vertebrae may cause the vertebra to return toward its initial orientation when it is released. At stage 142, the location of the bone anchor in the vertebra is adjusted to avoid the neural Interference. For example, the orientation of hole 81 can be modified. In another example, hole 81 is repaired with bone cement or other suitable material, and a new hole is formed in the vertebra to receive the bone anchor. In yet another example, a force is applied to another bone anchor to reposition the vertebra while the anchor indicating potential encroachment on neural elements is left alone. Procedure 130 returns to step 134 where the re-positioned anchor is engaged and manipulated to move the vertebra toward the aligned orientation with spinal column B while monitored with the nerve monitoring system.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present Invention and should not be construed to limit or restrict the Invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not Intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method comprising:
   preparing a bony tissue area of a vertebra for reception of a bone anchor when the vertebra is in a first position;
   electrically coupling a link of a nerve monitoring system to a bone anchor driver;
   engaging the bone anchor with the bone anchor driver to engage the bone anchor to the prepared bony tissue area of the vertebra while the link provides an electrical signal to the bone anchor through the bone anchor driver;
   detecting a neural element threshold as a function of the electrical signal with the nerve monitoring system while engaging the bone anchor to the bony tissue area;
   removing the bone anchor driver from the link;
   engaging the bone anchor with a correction tool;
   electrically coupling the correction tool with the link;
   moving the correction tool while engaged to the bone anchor to change an orientation of the vertebra to a second position from the first position; and
   providing an electrical signal through from the link to the bone anchor through the correction tool to the bone anchor to detect a neural element threshold as a function of the electrical signal with the nerve monitoring system while changing the orientation of the vertebra.

2. The method of claim 1, further comprising fixing the vertebra at the second position with a connecting element anchored to the bone anchor and extending to at least one other bone anchor engaged to a second vertebra.

3. A method comprising:
   providing a first bone anchor and a second bone anchor;
   engaging the first bone anchor to a first location on a first vertebral body of a spinal column when the first vertebral body is at a first orientation relative to the spinal column and engaging the second bone anchor to a second location on the spinal column;
   interconnecting the first bone anchor with the second bone anchor;
   coupling a correction tool to at least one of the first and second bone anchors to provide an electrical signal that travels through the correction tool to the at least one of the first and second bone anchors; and
   monitoring the proximity of the at least one of first and second bone anchors with a nerve monitoring system to detect interference with a neural element while the first vertebral body is moved from the first orientation toward a second orientation.

4. The method of claim 3, further comprising simultaneously monitoring the proximity of each of the first and second bone anchors relative to neural elements.

5. The method of claim 3, wherein the second location is on the first vertebral body.

6. The method of claim 3, wherein the second location is on a second vertebral body.

7. The method of claim 3, wherein the electrical signal allows the nerve monitoring system to monitor the proximity of the at least one of first and second bone anchors.

8. The method of claim 3, wherein the proximity of the at least one of first and second bone anchors is monitored by sending the electrical signal such that the electrical signal travels through the correction tool to the at least one of first and second bone anchors to monitor the proximity of the at least one of first and second bone anchors by detecting a neural element threshold as a function of the electrical signal.

9. The method of claim 3, wherein the first bone anchor is interconnected to the second bone anchor by a cross-link connecting element.

10. The method of claim 3, wherein:
    the first bone anchor is interconnected to the second bone anchor by a cross-link connecting element; and
    the second location is on the first vertebral body.

11. The method of claim 3, wherein the correction tool engages the first bone anchor and is spaced apart from the second bone anchor by a cross-link connecting element that interconnects the first bone anchor with the second bone anchor.

12. The method of claim 3, further comprising manipulating the correction tool to move the first vertebral body from the first orientation to the second orientation by applying a rotational force to the correction tool to rotate the correction tool and correspondingly rotate the first vertebral body toward the second orientation.

13. The method of claim 12, wherein the second location is on the first vertebral body.

14. The method of claim 12, wherein:
    the second location is on a second vertebral body; and
    the rotational force is translated to the second bone anchor to rotate the second vertebral body such that the second vertebral body is aligned with the spinal column.

15. A method comprising:
engaging a first bone anchor to a first location on a first vertebral body of a spinal column when the first vertebral body is at a first orientation relative to the spinal column;
engaging a second bone anchor to a second location on the spinal column;
interconnecting the first bone anchor with the second bone anchor;
coupling a correction tool to the first bone anchor to provide an electrical signal that travels through the correction tool to the first bone anchor;
manipulating the correction tool to move the first vertebral body from the first orientation to a second orientation; and
monitoring the proximity of the first bone anchor with a nerve monitoring system to detect interference with a neural element while the first vertebral body is moved from the first orientation toward the second orientation.

16. The method of claim 15, wherein the electrical signal travels through the correction tool to the first bone anchor to monitor the proximity of the first bone anchor.

17. The method of claim 15, wherein the proximity of the first bone anchor is monitored by sending the electrical signal such that the electrical signal travels through the correction tool to the first bone anchor to monitor the proximity of the first bone anchor by detecting a neural element threshold as a function of the electrical signal.

18. The method of claim 15, wherein the second location is on the first vertebral body.

19. The method of claim 15, wherein:
the first bone anchor is interconnected to the second bone anchor by a cross-link connecting element; and
the second location is on the first vertebral body.

20. The method of claim 15, wherein the first bone anchor is interconnected to the second bone anchor by a cross-link connecting element that directly engages a head of the first bone anchor and a head of the second bone anchor.

* * * * *